(12) United States Patent  (10) Patent No.: US 9,702,838 B2
Ota et al.  (45) Date of Patent: Jul. 11, 2017

(54) METHOD FOR EVALUATION TESTING OF MATERIAL FOR INTERNAL COMBUSTION ENGINE

(71) Applicant: SUMITOMO ELECTRIC INDUSTRIES, LTD., Osaka-shi, Osaka (JP)

(72) Inventors: Hajime Ota, Osaka (JP); Taichiro Nishikawa, Osaka (JP); Kazuo Yamazaki, Neyagawa (JP); Masao Sakuta, Neyagawa (JP); Takeshi Tokuda, Neyagawa (JP)

(73) Assignee: SUMITOMO ELECTRIC INDUSTRIES, LTD., Osaka-shi, Osaka (JP)

( * ) Notice: Subject to any disclaimer, the term of this patent is extended or adjusted under 35 U.S.C. 154(b) by 259 days.

(21) Appl. No.: 14/655,154

(22) PCT Filed: Nov. 4, 2013

(86) PCT No.: PCT/JP2013/079800
§ 371 (c)(1),
(2) Date: Jun. 24, 2015

(87) PCT Pub. No.: WO2014/061830
PCT Pub. Date: Apr. 24, 2014

(65) Prior Publication Data
US 2015/0330922 A1 Nov. 19, 2015

(30) Foreign Application Priority Data

Dec. 25, 2012 (JP) .................... 2012-281639

(51) Int. Cl.
*G01N 25/04* (2006.01)
*C22C 19/05* (2006.01)
(Continued)

(52) U.S. Cl.
CPC ............. *G01N 25/04* (2013.01); *C22C 19/03* (2013.01); *C22C 19/05* (2013.01); *C22C 19/058* (2013.01);
(Continued)

(58) Field of Classification Search
CPC ....................................... G01N 25/04
(Continued)

(56) References Cited

U.S. PATENT DOCUMENTS

2009/0104070 A1* 4/2009 Ditze .................. C22B 7/003
420/409
2011/0290384 A1* 12/2011 Otsuki ................. C21D 5/00
148/614

FOREIGN PATENT DOCUMENTS

CN 101762452 A 6/2010
CN 102439184 A 5/2012
(Continued)

OTHER PUBLICATIONS

"Hydrochloric Acid + Sodium Chloride." Sandvik Materials Technology. Sandvik, n.d. Web. Apr. 26, 2017. http://smt.sandvik.com/en/materials-center/corrosion-tables/hydrochloric-acid-sodium-chloride/.*

*Primary Examiner* — Peter Macchiarolo
*Assistant Examiner* — Alexander Mercado
(74) *Attorney, Agent, or Firm* — Drinker Biddle & Reath LLP

(57) ABSTRACT

A sample composed of a nickel-based metal is immersed in a corrosive solution (aqueous solution containing an acid and sodium chloride). The sample that has been immersed in the corrosive solution is exposed to a flame of engine oil, and further heated. By immersing the sample in the particular corrosive solution, a Ni-enriched phase which is deficient in additional elements and in which the Ni concentration (Continued)

increases is formed in a surface layer region of the sample. By exposing the sample having the Ni-enriched phase to the flame of the engine oil, components in the engine oil are activated and brought into contact with the sample to form a low-melting point phase in the surface layer region of the sample. By heating the sample having the low-melting point phase to melt the low-melting point phase and resolidifying the low-melting point phase, particles and the like can be formed depending on the type of material of the sample. The ease of the generation of particles can be evaluated by using simple equipment instead of an engine for testing.

4 Claims, 12 Drawing Sheets

(51) Int. Cl.
| | | |
|---|---|---|
| *F02P 17/00* | (2006.01) | |
| *G01N 33/20* | (2006.01) | |
| *G01N 17/00* | (2006.01) | |
| *C22C 19/03* | (2006.01) | |
| *H01T 13/39* | (2006.01) | |
| *H01T 13/58* | (2011.01) | |

(52) U.S. Cl.
CPC .............. *F02P 17/00* (2013.01); *G01N 17/00* (2013.01); *G01N 33/20* (2013.01); *H01T 13/39* (2013.01); *H01T 13/58* (2013.01)

(58) Field of Classification Search
USPC .......................................... 73/114.01; 216/13
See application file for complete search history.

(56) References Cited

FOREIGN PATENT DOCUMENTS

| | | |
|---|---|---|
| CN | 102668283 A | 9/2012 |
| JP | H01-268836 A | 10/1989 |
| JP | H02-163336 A | 6/1990 |
| JP | H07-41893 A | 2/1995 |
| JP | 2002-286621 A | 10/2002 |
| JP | 2003-315253 A | 11/2003 |
| JP | 4413951 B2 | 2/2010 |
| JP | 2012-069393 A | 4/2012 |
| JP | 4921540 B2 | 4/2012 |
| WO | WO 2011/054561 A | 5/2011 |

\* cited by examiner

20 μm

20 μm

20 μm

20 μm

20 μm

20 μm

500 μm

500 μm

500 μm

500 μm

20 μm

20 μm

20 μm

20 μm

METHOD FOR EVALUATION TESTING OF MATERIAL FOR INTERNAL COMBUSTION ENGINE

TECHNICAL FIELD

The present invention relates to a method for evaluation testing of a material for an internal combustion engine, the method being used for evaluating characteristics of a metal material that constitutes a member included in an internal combustion engine or a raw material thereof, for example, an electrode of a spark plug included in an automobile engine or an electrode material. In particular, the present invention relates to a method for evaluation testing of a material for an internal combustion engine, the method being capable of being used for evaluating the ease of generation of particles that may be generated on a surface of a material with simple equipment.

BACKGROUND ART

An example of a part included in an internal combustion engine such as a gasoline engine of an automobile is a spark plug. Such a spark plug typically includes a cylindrical insulator, a main body metal fitting which holds the insulator, a rod-shaped center electrode which is held in the insulator and a leading end of which is exposed from an end of the insulator, a ground electrode that is welded to the main body metal fitting, and a terminal metal fitting disposed on another end of the insulator. The ground electrode is formed so as to have an L-shape and is attached to the main body metal fitting such that a short strip thereof faces an exposed end face of the center electrode. Nickel-based metals such as pure nickel and nickel alloys are used as the materials constituting the center electrode and the ground electrode.

One characteristic desired for a constituent member of an internal combustion engine, such as an electrode of the spark plug, and a raw material thereof is that particles are not easily generated on the surface of the constituent member or the raw material as a result of use over time (paragraphs [0010], [0011], etc. of the specification of PTL 1). These particles are formed as a result of a phenomenon in which the material constituting an electrode or the like is melted and then solidified in the form of spherical projections. The particles are composed of a mixture containing elements in an atmosphere, the elements being derived from engine oil or the like, and Ni (nickel), which forms a matrix of the electrode (paragraph [0010] of the specification of PTL 1). When a large number of such particles are generated on a surface of an electrode, in particular, when a large number of such particles are generated, and furthermore, grown to become coarse particles in a portion where spark discharge is performed (mainly on surfaces of the center electrode and the ground electrode that face each other), the ignition state of an engine may become unstable or, in the worst case, the particles may be detached and may damage the engine.

Accordingly, it is desirable to examine the ease of the generation of particles or the difficulty of the generation of particles. PTL 1 discloses equipment including a gasoline engine for testing, the equipment being used for examining the degree of the generation of particles (paragraph [0055] of the specification).

With regard to constituent members of an internal combustion engine and raw materials thereof, an engine for testing is usually used also in the case where characteristics other than the ease of the generation of particles are examined (for example, paragraph [0055] etc. of the specification of PTL 2).

CITATION LIST

Patent Literature

PTL 1: Japanese Unexamined Patent Application Publication No. 2012-069393

PTL 2: Japanese Patent No. 4413951

SUMMARY OF INVENTION

Technical Problem

It has been desirable to develop a method for examining the ease of the generation of particles by using simple equipment instead of special equipment such as an engine for testing. However, when examining characteristics of materials for internal combustion engines, in particular, the ease of the generation of particles, no evaluation methods using simple equipment have been hitherto investigated.

Accordingly, an object of the present invention is to provide a method for evaluation testing of a material for an internal combustion engine, the method being capable of evaluating, using simple equipment, the ease of the generation of particles, with respect to a material for an internal combustion engine, the material being composed of a nickel-based metal.

Solution to Problem

The inventors of the present invention collected a spark plug that had been used in an automobile, and obtained a sample in which a large number of particles 210 had been generated on a surface of an electrode of the spark plug and in which the surface was roughened, as shown in FIGS. 5A and 5B. Subsequently, the inventors of the present invention investigated a regeneration test of the generation state of such particles, in particular, a regeneration test using simple equipment. Conceivable examples of the simple equipment include a heating furnace and a combustion furnace. However, as described below, even when only heating or combustion was performed, a surface state similar to that of the electrode of the used spark plug which was actually collected was not obtained.

The composition of the electrode of the used spark plug that was actually collected was examined. As shown in FIG. 5C, a surface layer region 200 of a base material 100 composed of a nickel alloy was constituted by a composition different from the base material 100. Specifically, the surface layer region 200 was formed of a phase that is deficient in some of additional elements of the base material 100, in other words, a phase having a high concentration of Ni serving as a matrix (hereinafter referred to as "Ni-enriched phase"). A particle 210 was also mainly formed of this Ni-enriched phase. In addition, in the surface layer region 200 including the particle 210, a composite compound (typically, an oxide) 220 containing some elements among the additional elements of the base material 100 and some elements (such as Ca and P) that were believed to be contained in engine oil, and a compound (typically, an oxide) 222 containing some elements that were believed to be contained in the engine oil were present. Specifically, regions having a high concentration of components of the engine oil were locally present in the surface layer region 200.

Accordingly, a process that can produce the surface layer region 200 constituted by a composite component (or a mixture) that contains components (such as Ca and P) of engine oil and the Ni-enriched phase was examined. As a result, it was found that, in the case where a particular process that includes immersing a sample composed of a nickel-based metal in a particular corrosive solution, subsequently exposing the sample to a flame of engine oil, and further heating the sample was performed, the surface state was varied depending on the type of material of the sample. Specifically, regarding a material in which a large number of particles might be generated when actually used as an electrode of a spark plug, that is, regarding a sample composed of a material in which particles were easily generated, when the above particular process was conducted, a state where a large number of particles were generated on a surface of the sample and the surface was roughened or a state similar to this state was obtained. Regarding a sample composed of a material in which particles were not easily generated when actually used as an electrode of a spark plug, when the above particular process was conducted, particles were not easily generated or particles were not substantially generated. The reason that these results were obtained is believed to be as follows.

Recently, for the purpose of environmental preservation measures and the like, regarding automobile engines and the like, improvements in fuel efficiency have been attempted by performing exhaust gas recirculation (EGR), and idling stops are being performed. The inventors of the present invention found that when an idling stop is performed, the temperature of a constituent member of an internal combustion engine, such as an electrode of a spark plug, is decreased by stopping the engine to cause water condensation, and the constituent member comes into a state of being immersed in condensed water. It was also found that elements from the surroundings of the constituent member (typically, NOx components resulting from EGR) are mixed with the condensed water, and that a corrosive solution containing an acid may be generated. Therefore, when the number of times of ON/OFF of the engine is increased by idling stops, condensed water is repeatedly generated. By further performing EGR and the like, the above corrosive solution is repeatedly generated. If the duration of an engine stop is increased by idling stops, the constituent member of the internal combustion engine is immersed successively in a generated corrosive solution. It is believed that, in the long run, this corrosive solution permeates into the constituent member through, for example, grain boundaries of the crystal grains of a metal constituting the constituent member. It is believed that when the corrosive solution permeates and the metal constituting the member is corroded, a phase (the Ni-enriched phase in the nickel-based metal described above) which is deficient in additional elements in the metal and in which the concentration of the matrix increases is produced.

Meanwhile, when engine oil in an internal combustion engine is combusted together with gasoline, components (such as Ca and P) of the engine oil are activated in the combustion flame of the gasoline. More specifically, the components are believed to become ions or plasmas. Furthermore, it is believed that the following occurs: When Ca, P, etc. in such an active state contact the Ni-enriched phase, a low-melting point phase containing Ni and Ca, P, etc. is formed. During the ON state of the engine, the low-melting point phase is heated and the temperature thereof is increased, thereby being melted and flowing. During the OFF state of the engine, the temperature of the low-melting point phase is decreased and the low-melting point phase is solidified, thereby forming the particles described above and including the composite compound or the compound described above during the formation of the particles.

The flame of engine oil that can activate components of engine oil can be formed by using relatively simple equipment. In addition, equipment having a simple structure can also be used as equipment for immersing a sample in a corrosive solution and equipment for heating the sample. Accordingly, when evaluating the ease of the generation of the particles, with respect to a sample composed of a nickel-based metal, the testing method including a plurality of different steps of immersion in the particular corrosive solution, exposure to a flame of engine oil, and heating simulates an actual use environment, and the evaluation can be performed by this method using simple equipment. On the basis of the above findings, the present invention suggests that the above plurality of particular processes be conducted as a method for evaluating the ease of the generation of particles, with respect to a sample composed of a nickel-based metal.

The present invention relates to a method for evaluation testing of a material for an internal combustion engine, the method being used for evaluating characteristics of a metal material such as an electrode included in an internal combustion engine or a raw material of the electrode, and the method includes a wet etching step, a combustion step, and a heating step described below.

Wet etching step: The wet etching step is a step of preparing, as the metal material, a sample composed of a nickel-based metal, preparing, as a corrosive solution, an aqueous solution containing an acid and sodium chloride, and immersing the sample in the corrosive solution. In this step, a Ni-enriched phase is formed in a surface layer region of the sample.

Combustion step: The combustion step is a step of exposing the sample that has been immersed in the corrosive solution to a flame of engine oil. In this step, the Ni-enriched phase is brought into contact with a component in the engine oil to form a low-melting point phase in the surface layer region of the sample.

Heating step: The heating step is a step of heating the sample that has been exposed to the flame of the engine oil. In this step, the low-melting point phase is melted and resolidified.

The reagents such as the corrosive solution and the engine oil are easily available. It is sufficient that, in the wet etching step, an immersion tank to be filled with the corrosive solution is prepared, and in the combustion step, equipment that can form a flame of the engine oil is prepared. In the heating step, a common heating furnace can be used. Therefore, according to the method for evaluation testing of a material for an internal combustion engine of the present invention, the ease of the formation of particles (or the difficulty of the formation of particles) on a surface of a sample composed of a nickel-based metal can be evaluated by using simple equipment instead of an engine for testing. Furthermore, the method for evaluation testing of a material for an internal combustion engine of the present invention can be applied to any form of sample, such as a wire rod, a flat plate, or a formed body having a predetermined shape. Accordingly, it is not necessary to prepare a sample in the form of a final product such as a spark plug described in PTL 2. Only an electrode before assembling to, for example, a main body metal fitting of spark plug, or a raw material such as a wire rod or a flat plate before being formed into an electrode having a predetermined shape can be used as the sample. Therefore, in the method for evaluation testing of a material for an internal combustion engine of the present invention, the sample can also be easily prepared, and thus this method is a simple evaluation method. Furthermore, in the case where a raw material such as a wire rod for an electrode is used as a sample, the method for evaluation testing of a material for an internal combustion engine of the present invention can be used for selecting a raw material (the type of material) in which particles are not easily formed.

According to an embodiment of the present invention, the heating step may be performed in a non-oxidizing atmosphere at a heating temperature of 450° C. or more and less than 1,455° C. for a holding time of 1 hour or more and 100 hours or less.

By performing the heating step in a non-oxidizing atmosphere, the formation of an (excessive) oxide film in the heating step can be prevented, and heating energy in this step can be efficiently used for the generation of the particles, the enriched phase, and the like. In addition, by performing the heating step under the above particular conductions, the temperature and time that are sufficient for melting and flowing of the low-melting point phase can be ensured. Accordingly, for example, in the case where the sample is composed of a material that easily generates the particles, the particles are more easily generated and thus superiority and inferiority of the characteristics are expected to be easily evaluated. Therefore, in the above embodiment, the ease of the generation of particles can be evaluated with a higher accuracy.

According to an embodiment of the present invention, in the wet etching step, a solution containing at least one acid selected from hydrochloric acid, phosphoric acid, nitric acid, and sulfuric acid may be prepared as the corrosive solution, and an immersion time of the sample may be 2 hours or more and 48 hours or less.

The acids listed above are acids that may be generated in an actual use environment, such as an internal combustion engine of a gasoline engine. Accordingly, the corrosive solution containing at least one of the above acids simulates a corrosive solution that may be generated in the actual environment. Furthermore, by controlling the immersion time of the corrosive solution to the above specific range, the Ni-enriched phase can be sufficiently generated. Accordingly, for example, in the case where the sample is composed of a material that easily generates the particles, the particles are more easily generated and thus superiority and inferiority of the characteristics are expected to be easily evaluated. Therefore, in the above embodiment, the ease of the generation of particles can be evaluated with a higher accuracy.

According to an embodiment of the present invention, the method may further include, before the wet etching step, a heat treatment step of performing heat treatment on the sample. In the heat treatment step, a heating temperature may be 800° C. or more and 1,100° C. or less, and a holding time may be 1 hour or more and 200 hours or less.

While an engine is in the ON state, a constituent member of an internal combustion engine, such as an electrode of a spark plug, is exposed to a high-temperature environment (environment at 800° C. or more, and furthermore, 900° C. or more). While the engine is in the OFF state, as described above, the corrosive solution is generated and the constituent member of the internal combustion engine may contact the corrosive solution. Accordingly, it is believed that the embodiment that includes the wet etching step after the heat treatment step more accurately simulates the actual environment that "holding of a high-temperature state during the ON state of an engine contact with a corrosive solution that may be generated after the engine turns to the OFF state".

Advantageous Effects of Invention

According to the method for evaluation testing of a material for an internal combustion engine of the present invention, the ease of the formation of particles in a material for an internal combustion engine can be evaluated with simple equipment.

REFERENCE SIGNS LIST

Figure 1A:
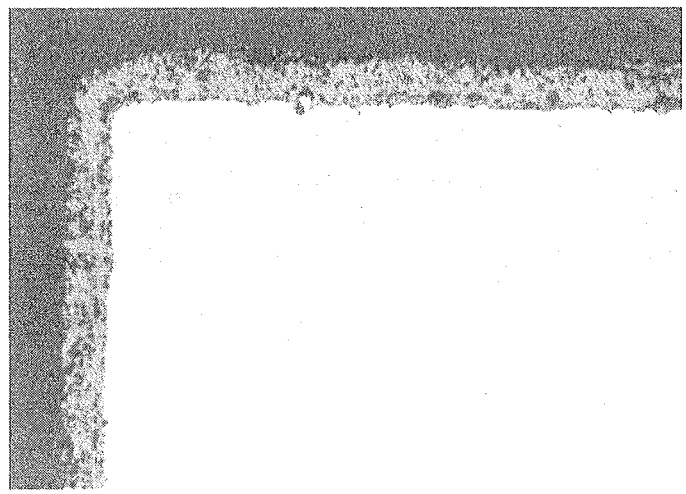
FIG. 1A is an optical microscope photograph of a cross section showing a state after each step when a method for evaluation testing of a material for an internal combustion engine of the present invention is applied, and shows a state of Sample No. 1 after a wet etching step.

100 base material, 200 surface layer region, 210 particle, 220 composite compound, 222 compound

DESCRIPTION OF EMBODIMENTS

The present invention will now be described in more detail. First, a test object will be described.

(Test Object)

Examples of test objects include those composed of metal materials, such as constituent members (e.g., electrodes) of parts (e.g., spark plugs) included in an internal combustion engine, and raw materials (e.g., electrode materials) used for the constituent members. In particular, a method for evaluation testing of a material for an internal combustion engine of the present invention can be suitably used for evaluating characteristics of a metal material composed of a nickel-based metal such as pure nickel or a nickel alloy, the metal material being used as an electrode of a spark plug or an electrode material serving as a raw material of the electrode.

Specific examples of the nickel alloy include alloys containing at least one element selected from Al, Si, Cr, Y, Ti, Mn, Fe, Nb, Ta, Mo, Cu, Nd, Zr, Ir, Yb, V, and the like as additional elements, and the balance being Ni and inevitable impurities. When the alloy contains Ni as a main component (97% by mass or more), it is possible to obtain an electrode for a spark plug which has good plastic workability and a low specific resistance (high electric conductivity) and whose wear due to sparks is suppressed. The smaller the content of the additional elements and the larger the content of Ni (for example, the Ni content being 98% by mass or more), the lower the specific resistance can be. With an increase in the content of the additional elements, the resistance to oxidation at high temperatures and the corrosion resistance are further improved. Accordingly, by preparing a sample composed of such a nickel alloy and evaluating the ease of the generation of particles of the sample, more preferable materials that are used as an electrode for a spark plug and electrode materials can be selected. Examples of the inevitable impurities include C and S. A certain amount of C is contained in some cases.

The form of the test object is not particularly limited. For example, in the case where the test object is composed of the above raw material, examples of the form of the test object include wire rods (typically, round wires and rectangular wires) and plate materials. In this case, a strip prepared by cutting any of the wire rods and plate materials to have an appropriate length is preferably used as a sample. For example, a product used as the constituent member, that is, a formed body produced by forming the above raw material to have a desired shape may be used as a sample without further treatment.

(Method for Evaluation Testing)

A method for evaluation testing of a material for an internal combustion engine of the present invention includes the steps of preparation of a sample→preparation of a corrosive solution and immersion in the corrosive solution→ combustion with a flame of engine oil→heating. After this heating step, by observing a surface or a cross section of the sample either visually or by using an appropriate microscope or the like, the ease of the generation of particles is evaluated. Prior to the immersion in the corrosive solution, heat treatment may be separately performed on the sample.

Preparation of Sample

First, as described above, a sample composed of an appropriate nickel-based metal is prepared.

Heat Treatment

In the case where a heat treatment step of heating the prepared sample at a high temperature is provided, crystal grains forming at least a surface layer region of the sample can be grown and coarsened in this step. Specifically, at least the surface layer region of the sample can have a coarse crystal structure, in other words, a simple structure in which the total length of the crystal grain boundaries is short. It is believed that, as a result, a corrosive solution described below can easily permeate into the sample. Accordingly, it is expected that, for example, in the case where the sample is composed of a material that easily generates the particles, the Ni-enriched phase and the particles are more easily generated, and the degree of the ease of the generation of the particles is easily recognized and easily evaluated.

This heat treatment simulates a high-temperature environment in an internal combustion engine such as a gasoline engine of an automobile. Accordingly, the heating temperature of the heat treatment step is, for example, 800° C. or more and 1,100° C. or less. The higher the heating temperature, the more easily crystal grains are coarsened. However, when the heating temperature is excessively high, for example, in the case where the atmosphere of this heat treatment is an oxygen-containing atmosphere, an oxide film may be excessively formed and may inhibit the permeation of the corrosive solution. Therefore, the heating temperature of the heat treatment step is more preferably 900° C. or more and 1,000° C. or less.

The holding time at the heating temperature can be appropriately selected and is, for example, one hour or more. An excessively long holding time causes an increase in the testing time, and thus the holding time is preferably 200 hours or less, and more preferably 100 hours or less. When the holding time is about 2 hours or more and about 24 hours or less, the heat treatment step is easily used and the testing time can be shortened. Preferably, the heating temperature and the holding time of the heat treatment step are mutually adjusted in accordance with the type of material of the sample, the atmosphere, etc.

The atmosphere of the heat treatment step is, for example, an oxygen-containing atmosphere. According to an examination results of an electrode of a used spark plug collected from an automobile, an oxide film is usually formed on a surface of the electrode. Accordingly, when the heat treatment step is performed in an oxygen-containing atmosphere, an oxide film can be efficiently formed on a surface of the sample in the heat treatment step. Thus, it is believed that the actual environment is more accurately simulated. Due to the coarsening of the crystal grains, the formed oxide film tends to have a multilayer structure in which a sparse layer composed of a coarse oxide is disposed on the inside of the sample and a dense layer composed of a relatively dense oxide is disposed on the outermost surface side of the sample.

A specific example of the oxygen-containing atmosphere is an air atmosphere. An air atmosphere is easily used because the atmosphere is easily controlled. Alternatively, the oxygen-containing atmosphere may be a low oxidizing atmosphere having a lower oxygen concentration than the air. A specific example of the oxygen concentration is 0.01% by volume or more and 20% by volume or less. In general, the atmosphere in an internal combustion engine such as a gasoline engine of an automobile has a lower oxygen concentration than the air (20% by volume or less). Accordingly, an embodiment in which the oxygen-containing atmosphere is a low oxidizing atmosphere simulates a state closer to the actual environment. Examples of the atmosphere gas other than oxygen include inert gases such as nitrogen, argon, and helium. The low oxidizing atmosphere can be formed by a mixed gas obtained by mixing oxygen gas and any of the inert gases, a mixed gas obtained by mixing oxygen gas, any of the inert gases, and the air, or the like. In the case where an oxide film is positively formed, preferably, the heating temperature, the holding time, the oxygen concentration in the atmosphere, and the like are mutually adjusted. For example, in the case of an air atmosphere, the heating temperature may be 900° C. or more and 1,000° C. or less, and the holding time may be 1 hour or more and 100 hours or less, furthermore, 1 hour or more and 72 hours or less, and in particular, 2 hours or more and 24 hours or less.

In the method for evaluation testing of a material for an internal combustion engine of the present invention, the formation of an oxide film in the heat treatment step before wet etching is not essential. Therefore, the atmosphere in the heat treatment step may be a non-oxygen atmosphere. Examples of the non-oxygen atmosphere include an atmosphere having an oxygen concentration of less than 0.01% by volume (typically a vacuum atmosphere) and the inert gas atmosphere described above. Note that, even in a vacuum atmosphere, as described above, an oxide film may be formed by maintaining a state where heating is conducted at a high temperature of 800° C. or more, and furthermore, 900° C. or more for a long time, for example, one hour or more. Accordingly, the present invention allows the presence of an oxide film on a sample before wet etching.

In this heat treatment step, a heating furnace (for example, an air atmosphere furnace or a vacuum furnace) with the above desired atmosphere can be used. After the above holding time passes, the sample may be cooled to room temperature. Alternatively, the sample may be provided to a subsequent wet etching step in a state where the sample is maintained at a desired temperature (for example, about 50° C. or more and 80° C. or less). As described below, when the sample is in a predetermined heated state, an effect of accelerating, for example, permeation of a corrosive solution can be expected, and a reduction in the testing time can be realized.

Preparation of Corrosive Solution and Immersion in Corrosive Solution

A wet etching step is a step of immersing the sample prepared as described above or the sample that has been further subjected to a heat treatment in a corrosive solution described below to generate, in a surface layer region of the sample, a phase which is deficient in additional elements and in which the quantity of the additional elements is decreased, that is, a Ni-enriched phase. Note that, in the case where the sample is composed of a material having a low content of additional elements, such as pure nickel, it is allowed that the composition of the surface layer region is not substantially changed before and after the wet etching step (the Ni-enriched phase is already present before the wet etching step).

In the wet etching step, first, a corrosive solution is prepared. The corrosive solution mainly contains water so as to simulate condensed water. When the corrosive solution contains chloride ions ($Cl^-$), corrosion can be accelerated and the testing time can be effectively reduced. Accordingly, the corrosive solution is an aqueous solution containing chloride ions ($Cl^-$). In particular, in order to use a neutral aqueous solution as a base, an aqueous sodium chloride (NaCl) solution is used. The concentration (mass ratio) of NaCl in the aqueous NaCl solution can be appropriately selected. An aqueous NaCl solution having a NaCl concentration of 1% or more and 10% or less is easily used. It is believed that, in this range, NaCl does not easily become a main factor of corrosion.

Furthermore, the corrosive solution contains an acid. It is believed that, in the case where the above-described EGR is performed, nitric acid due to NOx contained in exhaust gas may be generated. According to examination results obtained by the inventors of the present invention, elements such as S (sulfur) and P (phosphorus) were detected in an electrode of a used spark plug collected from an automobile. Conceivably, S is derived from impurities in gasoline and P is derived from impurities in engine oil. It is believed that sulfuric acid may be generated due to S and phosphoric acid may be generated due to P. Furthermore, it is believed that hydrochloric acid may be generated due to a chloride contained in a constituent member of the internal combustion engine. As described above, in an environment where an internal combustion engine such as a gasoline engine is used, various types of acids may be generated, and thus it is proposed that the corrosive solution contain an acid in addition to NaCl. In particular, the acid is preferably at least one acid selected from hydrochloric acid, phosphoric acid, nitric acid, and sulfuric acid described above because the resulting corrosive solution becomes similar to a corrosive solution that may be generated in the actual environment. It is expected that the use of a single acid facilitates the preparation and adjustment of the concentration, and that the use of a plurality of acids in combination simulates a corrosive solution more similar to a corrosive solution that may be generated in the actual environment.

The concentration of the acid can be appropriately selected. When the total mass of the corrosive solution is assume to be 100, a ratio represented by the mass of aqueous NaCl solution:the mass of acid=about 50:50 to 99:1 is easily used, though it depends on the type of acid. It is expected that, in the range of this ratio, corrosion can be sufficiently performed by an immersion for a relatively short time (about 2 hours or more and 48 hours or less). The temperature of the corrosive solution may be room temperature (about 20° C. to 25° C.). When the temperature of the corrosive solution is about 50° C. or more and 80° C. or less, corrosion can be further accelerated and the immersion time can be reduced.

The immersion time can be appropriately selected in accordance with the environment to be simulated, the type of material of the sample, the composition of the corrosive solution (acid concentration and NaCl concentration), the temperature, etc., and is, for example, 2 hours or more and 48 hours or less. In particular, an immersion time of 5 hours or more and 24 hours or less is easily used, and the testing time can be reduced in this range.

The corrosive solution is preferably put in an appropriate immersion tank. The immersion tank may be housed in a thermostatic chamber and the immersion may be performed in this state. In this case, the temperature of the corrosive solution is easily maintained at a desired temperature. The sample is immersed in the corrosive solution for a certain period of time, then taken out from the corrosive solution, and dried.

Combustion with Flame of Engine Oil

A combustion step is a step of generating mainly a low-melting point phase and the like in the surface layer region of the sample that has been subjected to the wet etching step. In general, engine oil contains elements such as Ca (calcium), P (phosphorus), and K (potassium). These elements are present in the form of a compound such as an oxide or a composite oxide as described above, and mainly included in the Ni-enriched phase. It was found that, in order to form such a structure, the Ni-enriched phase needs to be in a state of being easily melted, and for this purpose, it is suitable that a sample be exposed to a flame of engine oil. The reason for this is believed to be as follows. By forming a flame of engine oil, components (the elements mentioned above) in the engine oil can be activated, specifically, ionized or formed into plasma. When Ca and P in such an active state contact the Ni-enriched phase, these elements can generate a low-melting point phase (alloy phase) that contains Ni and Ca, P, etc. or can easily bond with oxygen in the atmosphere to produce a (composite) oxide. In other words, in order to generate, for example, a low-melting point phase having a lower melting point than Ni, elements in engine oil need to be activated. Accordingly, the inventors of the present invention also examined other methods such as ion implantation. However, by using a flame of engine oil, components of the engine oil can be activated with simple equipment. Therefore, a flame of engine oil is used in the present invention.

Commercially available products containing Ca, P, K, etc. can be used as the engine oil used in the combustion step. In particular, when engine oil having a high content of Ca, P, K, etc., for example, engine oil for ships is used, the amount of elements that are activated can be further increased. Specifically, it is expected that the amount of active elements that can contact the Ni-enriched phase can be increased and the low-melting point phase and the like can be more easily produced.

In this combustion step, equipment that can form a flame of engine oil can be appropriately used. An example of the equipment that can be used includes an explosion-proof enclosure, an introduction portion that introduces engine oil in the explosion-proof enclosure, and an ignition portion that ignites the engine oil introduced from the introduction portion to form a flame.

In addition to the exposure of a sample to a flame of engine oil, the engine oil may further be applied onto a surface of the sample in advance. By igniting the formed flame on the applied engine oil to further form a flame, the surface of the sample can be more reliably exposed to the flame.

Heating

A heating step is a step of heating the sample in which a low-melting point phase and the like are formed by being exposed to a flame of engine oil to melt the low-melting point phase, to allow to flow the low-melting point phase, and to incorporate a compound such as a (composite) oxide containing elements in the engine oil. When the melted low-melting point phase flows and is then cooled, the low-melting point phase is resolidified on a surface of the sample and forms particles, voids are formed in the sample due to the flow of the low-melting point phase, or the melted low-melting point phase becomes in a state including the above (composite) oxide. Components (the elements such as Ca, P, and K mentioned above) of the engine oil may be contained in the voids. Furthermore, it is believed that the components of the sample are forcibly moved to the surface layer side as a result of the formation of the voids, spherical projections and the like are formed on the surface of the sample, and consequently, irregularities are formed. In order to form particles and to form voids by allowing the low-melting point phase to flow, the sample needs to be heated to a certain degree. Therefore, in the heating step, the heating temperature is preferably 450° C. or more and less than 1,455° C., and the holding time is preferably 1 hour or more and 100 hours or less. The heating step is preferably performed in a non-oxidizing atmosphere.

When the heating step is performed in a non-oxidizing atmosphere, oxidation and the like of the surface of the sample can be prevented, heating energy of this step can be efficiently used for melting, flowing, etc. of the low-melting point phase, and the particles, the voids, and the like can be easily formed. As a result, superiority and inferiority of the ease of the generation of the particles can be easily evaluated. Examples of the non-oxidizing atmosphere include the vacuum atmosphere and the inert gas atmosphere described above.

When the heating temperature of the heating step is 450° C. or more, melting, flowing, etc. of the low-melting point phase can be satisfactorily performed. When the heating temperature of the heating step is less than 1,455° C., which is the melting point of Ni, melting of Ni does not occur, and only melting of the low-melting point phase having a lower melting point than Ni can be efficiently caused. When the holding time of the heating step is one hour or more, the time for melting, flowing, etc. of the low-melting point phase can be sufficiently ensured. When the holding time of the heating step is 100 hours or less, the excess of the testing time can be prevented. When the low-melting point phase is heated at a high temperature as described above, for example, constituent elements of the low-melting point phase are sequentially precipitated in a cooling step, and thus the low-melting point phase can be separated.

In this heating step, a heating furnace (for example, a vacuum furnace) with the above desired atmosphere can be used.

The heating of this heating step is preferably started after a sample is exposed to a flame of engine oil and then placed in a heating furnace. Alternatively, in the case where the explosion-proof enclosure can keep the temperature of the sample hot or includes a mechanism that can perform heating, the heating may be started immediately before the sample is exposed to a flame, or the heating may be started in the course of the exposure to a flame.

Evaluation

Typically, the sample that has been subjected to the heating step is cooled to room temperature, and the ease of the formation of particles is then evaluated. Examples of the evaluation include observation of the appearance of the sample, and observation of a cross section of the sample with a microscope (the presence or absence of voids and composition analysis in the surface layer region and in the vicinity of the voids). Superiority and inferiority of the ease of the formation of particles can be evaluated by the presence or absence of particles, the presence or absence of voids, etc. Specifically, materials which have particles and voids, and furthermore, materials which have a large number of particles, a large number of voids, or large voids can be evaluated as materials in which particles are easily formed. In contrast, materials which do not have particles and voids, materials which have a small number of particles and a small number of voids, and materials which do not substantially have particles and which have small voids can be evaluated as materials in which particles are not easily formed.

Alternatively, a sample serving as a reference (hereinafter referred to as "reference sample") may be prepared, and the observation of the appearance and the observation of a cross section with a microscope may be performed by using both the reference sample and a sample of the test object. Thus, superiority and inferiority of the two samples can be evaluated by comparing the results of the samples. In this case, with respect to both the reference sample and the sample of the test object, absolute value data of the size and the number of generation of particles, the size and the number of generation of voids, and the like are preferably measured and compared. By performing this evaluation, a material in which particles are not easily formed can be selected on the basis of the reference sample.

Test Example 1

The validity of the method for evaluation testing of a material for an internal combustion engine of the present invention will be examined by using a specific test example.

A nickel alloy electrode material which has been used as a raw material of an electrode of a spark plug included in a gasoline engine of an automobile was prepared as a sample. In this test, rectangular wire rods composed of a nickel alloy containing, in terms of mass %, 0.35% of Y, 0.25% of Si, and the balance being Ni and inevitable impurities were prepared as Sample Nos. 1 and 100. Rectangular wire rods composed of a nickel alloy containing, in terms of mass %, 1.5% of Si, 1.5% of Cr, and 2% of Mn, and the balance being Ni and inevitable impurities were prepared as Sample Nos. 2 and 200. These rectangular wire rods were each produced by a known manufacturing method and under known manufacturing conditions (melting/casting→hot working→cold working→softening).

Figure 5A:
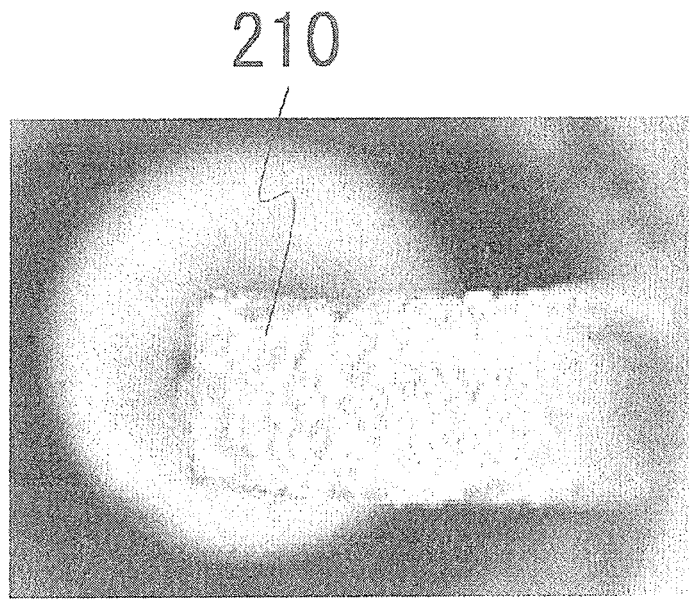
FIG. 5A is a side face photograph showing an appearance of an electrode of a used spark plug collected from an automobile.
Figure 5B:
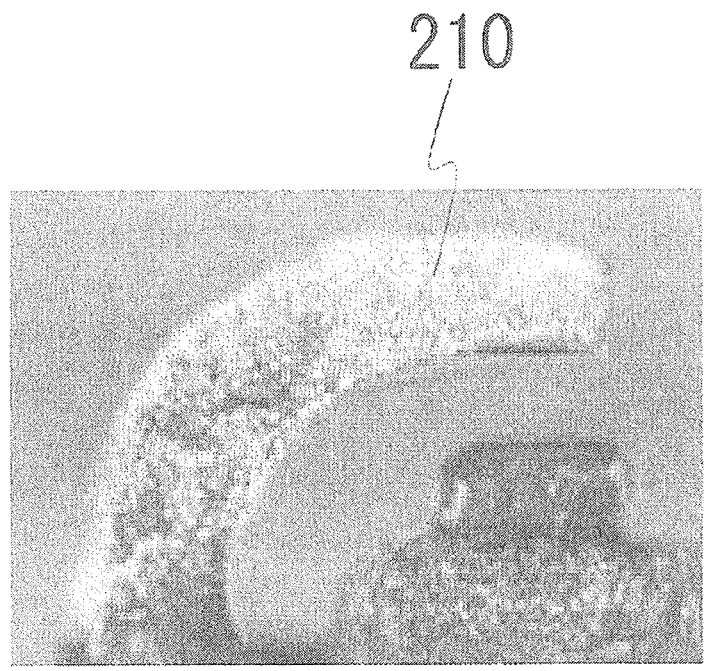
FIG. 5B is a front face photograph showing an appearance of an electrode of a used spark plug collected from an automobile.
Figure 5C:
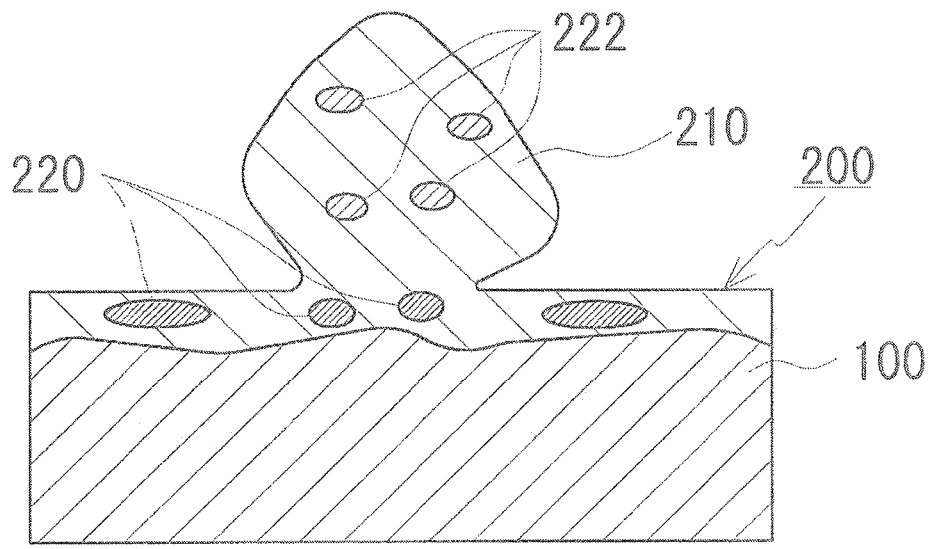
FIG. 5C is an explanatory view that schematically shows a surface layer region of an electrode of a used spark plug collected from an automobile.

Sample Nos. 1 and 100 are samples composed of a material in which particles are easily formed compared with Sample Nos. 2 and 200. It had been confirmed that, in the case where the rectangular wire rods of Sample Nos. 1 and 100 were each formed into an electrode and used in a spark plug of a gasoline engine of an automobile, particles shown in FIGS. 5A and 5B were formed on a surface of the electrode with time (refer to Sample No. 122 of PTL 1). In contrast, Sample Nos. 2 and 200 are samples composed of a material in which particles are not easily formed compared with Sample Nos. 1 and 100. It has been confirmed that, in the case where the rectangular wire rods of Sample Nos. 2 and 200 were each formed into an electrode and used in a spark plug of a gasoline engine of an automobile, particles were not easily formed on a surface of the electrode for a long period of time.

Sample Nos. 100 and 200 are each a sample used for conducting a comparative test. Here, in the comparative test, each of the samples was exposed to a flame of commercially available engine oil for ships and then heated. The step of combusting the samples by exposing the samples to a flame of engine oil was conducted by using equipment including an explosion-proof enclosure, an introduction portion that introduces engine oil in the explosion-proof enclosure, and an ignition portion that ignites the engine oil introduced from the introduction portion to form a flame. The step of heating the samples after the step of combustion was conducted by using a vacuum furnace in a vacuum atmosphere (oxygen content: 0.01% by volume or less, the degree of vacuum: 50 Pa or less) at 900° C. for 70 hours.

Figure 6A:
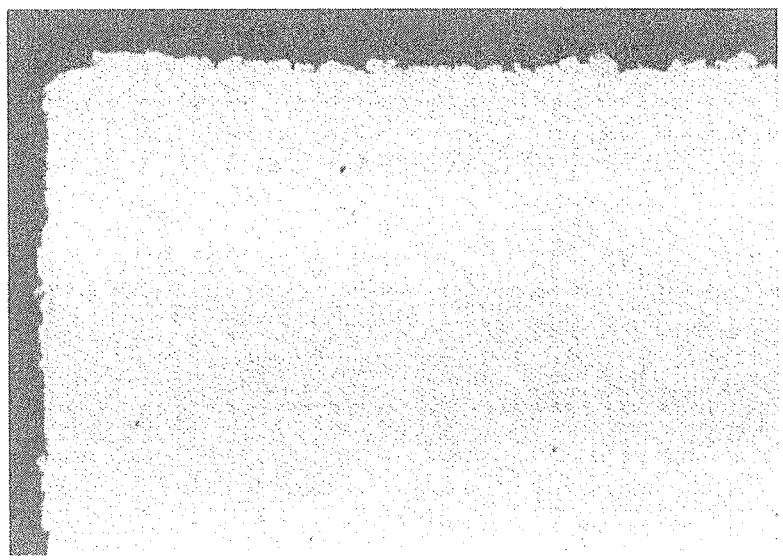
FIG. 6A is an optical microscope photograph of a cross section showing a state after each step when a comparative test is applied, and shows Sample No. 100 before the test.
Figure 6B:
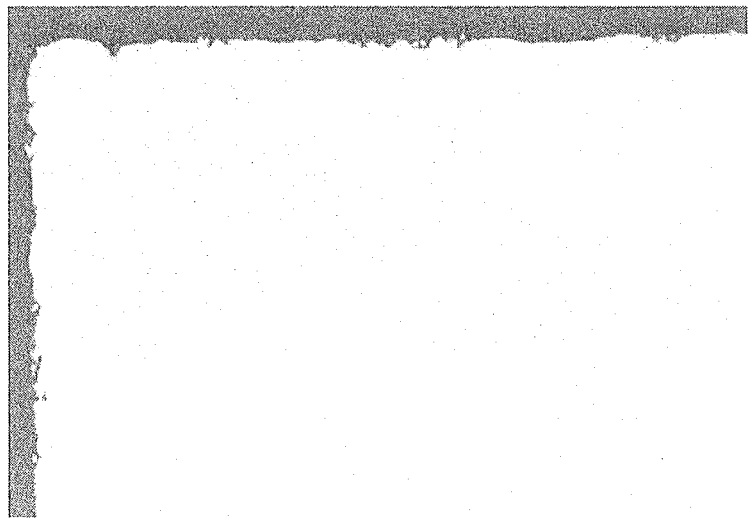
FIG. 6B is an optical microscope photograph of a cross section showing a state after each step when a comparative test is applied, and shows Sample No. 100 after combustion.
Figure 6C:
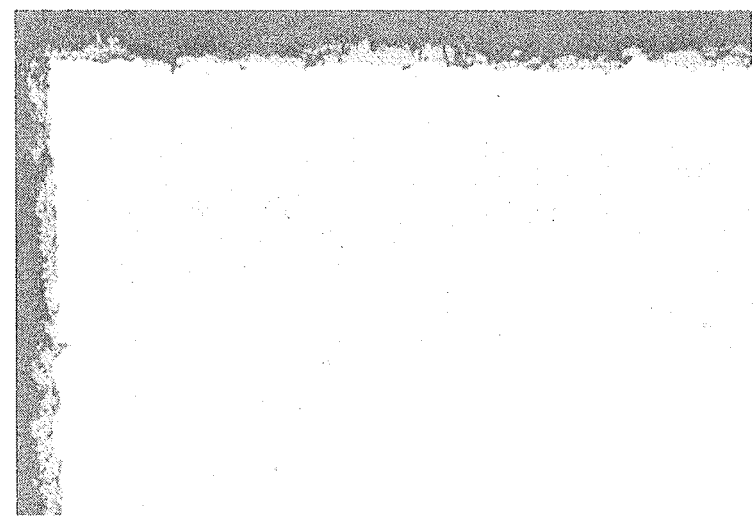
FIG. 6C is an optical microscope photograph of a cross section showing a state after each step when a comparative test is applied, and shows Sample No. 100 after heating.
Figure 6D:
FIG. 6D is an optical microscope photograph of a cross section showing a state after each step when a comparative test is applied, and shows Sample No. 200 before the test.
Figure 6E:
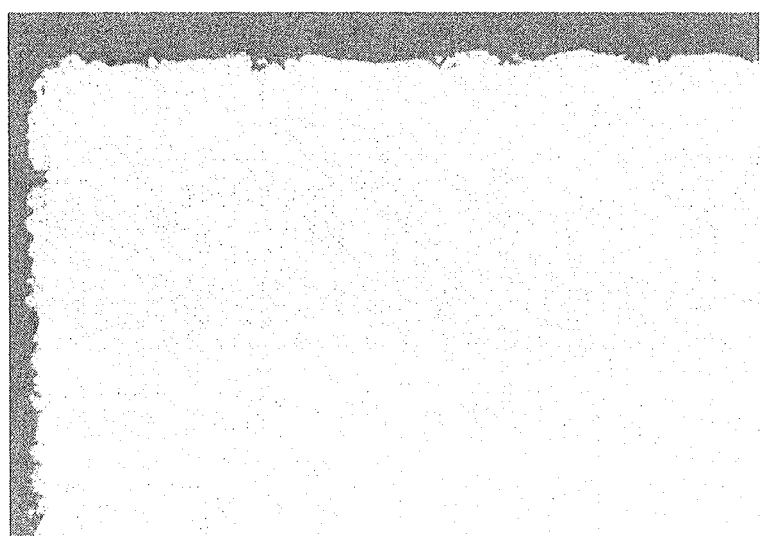
FIG. 6E is an optical microscope photograph of a cross section showing a state after each step when a comparative test is applied, and shows Sample No. 200 after combustion.
Figure 6F:
FIG. 6F is an optical microscope photograph of a cross section showing a state after each step when a comparative test is applied, and shows Sample No. 200 after heating.

Regarding Sample Nos. 100 and 200, each of the rectangular wire rod before the comparative test, the rectangular wire rod after the combustion by the exposure to a flame of the engine oil, and the rectangular wire rod cooled to room temperature after further heating was cut with a cross-section polisher (CP) and a cross section was obtained. Each of the cross sections was observed with an optical microscope. FIGS. 6A to 6C are microscope photographs of Sample No. 100 before the test, after combustion, and after heating, respectively. FIGS. 6D to 6F are microscope photographs of Sample No. 200 before the test, after combustion, and after heating, respectively. Note that, in FIGS. 6A and 6D, irregularities of the samples are roughened portions due to cutting of the rectangular wire rod. After the combustion, and furthermore, even after the heating, the irregularities, which are roughened portions due to cutting, are substantially maintained. This point also applies to FIGS. 1A to 1F.

Regarding Sample No. 100, as shown in FIGS. 6A and 6B, there is no substantial difference in the surface layer region between before and after the combustion. As shown in FIG. 6C, even when heating is further performed after the combustion, only an oxide film (a Γ-shaped dark gray portion formed on a rectangular light gray portion (base material)) is somewhat formed on the surface of the sample. Similarly, regarding Sample No. 200, as shown in FIGS. 6D and 6E, there is no substantial difference in the surface layer region between before and after the combustion. As shown in FIG. 6F, even when heating is further performed after the combustion, only an oxide film (a Γ-shaped dark gray portion formed on a rectangular light gray portion (base material)) is somewhat formed on the surface of the sample. That is, these results show that, with the comparative test (combustion with a flame of engine oil→heating) or only the combustion with a flame of engine oil, an evaluation of characteristics cannot be performed to the extent that Sample No. 100 and Sample No. 200 can be distinguished from each other. In particular, although Sample No. 100 is originally composed of a material in which particles may be generated, only an oxide film is formed as described above. It has also been confirmed that, in the case where only the heating is conducted under the conditions described above without conducting the combustion with a flame of engine oil, only an oxide film is somewhat formed on the surface of each of the samples, as shown in FIGS. 6C and 6F. These results show that the ease of the formation of particles cannot be appropriately evaluated by any of only the heating, only the combustion, and the comparative test including the combustion and the subsequent heating.

Sample Nos. 1 and 2 are samples each subjected to a test including steps of heat treatment step→wet etching step→combustion step→heating step in that order. The heat treatment step was performed by using an air atmosphere furnace in an air atmosphere at 900° C. for 24 hours. CP cross sections of Sample Nos. 1 and 2 that were subjected to the heat treatment step and then cooled to room temperature were obtained as in Sample Nos. 100 and 200, and each of the cross sections was observed with a scanning electron microscope (SEM). According to the results, it was confirmed that, in each of Sample Nos. 1 and 2, only an oxide film having a larger thickness than Sample Nos. 100 and 200 was formed. On the basis of these results and the heating conditions for Sample Nos. 100 and 200, the ease of the formation of particles cannot be appropriately evaluated by conducting only simple heating in a vacuum atmosphere or in an air atmosphere.

Figure 1B:
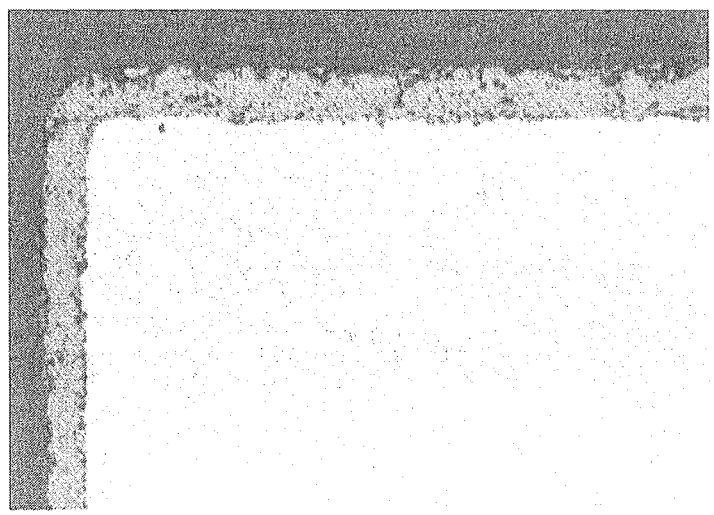
FIG. 1B is an optical microscope photograph of a cross section showing a state after each step when a method for evaluation testing of a material for an internal combustion engine of the present invention is applied, and shows a state of Sample No. 1 after a combustion step.
Figure 1C:
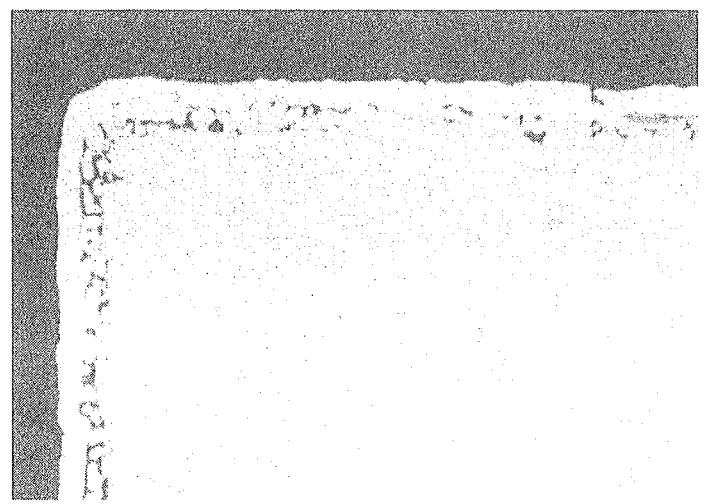
FIG. 1C is an optical microscope photograph of a cross section showing a state after each step when a method for evaluation testing of a material for an internal combustion engine of the present invention is applied, and shows a state of Sample No. 1 after a heating step.
Figure 1D:
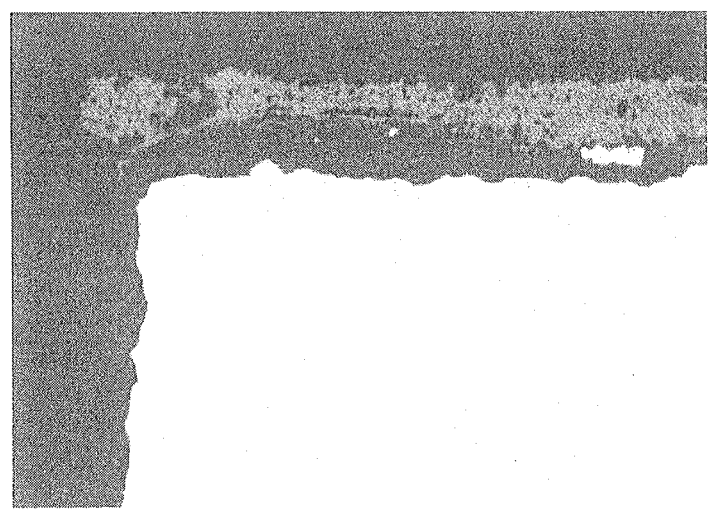
FIG. 1D is an optical microscope photograph of a cross section showing a state after each step when a method for evaluation testing of a material for an internal combustion engine of the present invention is applied to each of Sample No. 1 and Sample No. 2 that are composed of different materials, and shows a state of Sample No. 2 after a wet etching step.

In the etching step, an aqueous NaCl solution containing phosphoric acid and nitric acid was prepared as a corrosive solution. In this test, phosphoric acid, nitric acid, and an aqueous NaCl solution were prepared and mixed so that a ratio represented by phosphoric acid:nitric acid:5 mass % aqueous sodium chloride solution was 5:5:90 in terms of mass ratio. The prepared corrosive solution was heated to 80° C., and Sample Nos. 1 and 2 that had been subjected to the heat treatment step (and that had been cooled to room temperature in this test) were immersed in the corrosive solution in this state and maintained for 15 hours. After immersion for 15 hours, Sample Nos. 1 and 2 were washed with water and CP cross sections of Sample Nos. 1 and 2 were then obtained. Each of the cross sections was observed with an optical microscope. FIG. 1A shows a microscope photograph of the cross section of Sample No. 1 after the wet etching step. FIG. 1D shows a microscope photograph of the cross section of Sample No. 2 after the wet etching step.

As shown in FIGS. 1A and 1D, in each of Sample Nos. 1 and 2, an oxide film (in Sample No. 1, a Γ-shaped dark gray portion, and in Sample No. 2, a quadrangular dark gray portion formed on a rectangular light gray portion (base material)) is formed on the surface of the sample. With regard to Sample Nos. 1 and 2, although there is a somewhat difference in the state of the presence the oxide film, there is no significant difference in the surface state. These results show that the ease of the formation of particles cannot be appropriately evaluated by simply immersing a sample in the corrosive solution (after the heat treatment step described above). In Sample No. 2, the quadrangular dark gray portion (oxide film) is present only above the rectangular light gray portion (base material), and a black region is observed between the base material and the oxide film. An oxide film is not present in this black region. The reason for this is believed that Sample No. 2 is composed of a material in which an oxide film is detached more easily than Sample No. 1 in the case where Sample Nos. 1 and 2 are subjected to the heat treatment under the same conditions and then immersed in the corrosive solution.

Figure 1E:
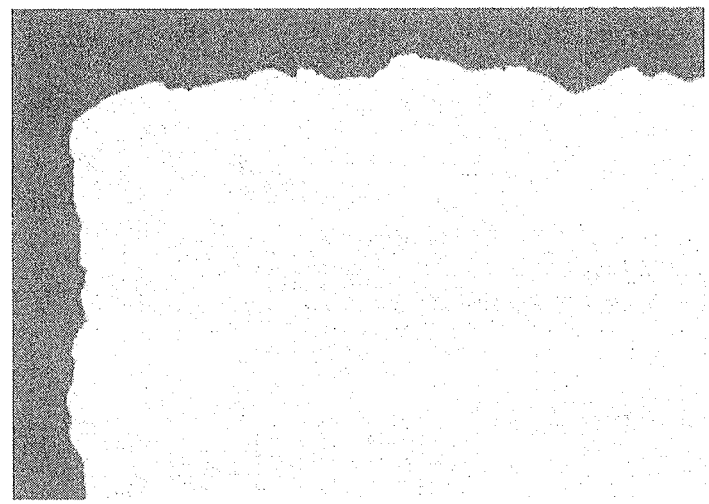
FIG. 1E is an optical microscope photograph of a cross section showing a state after each step when a method for evaluation testing of a material for an internal combustion engine of the present invention is applied, and shows a state of Sample No. 2 after a combustion step.
Figure 2B:
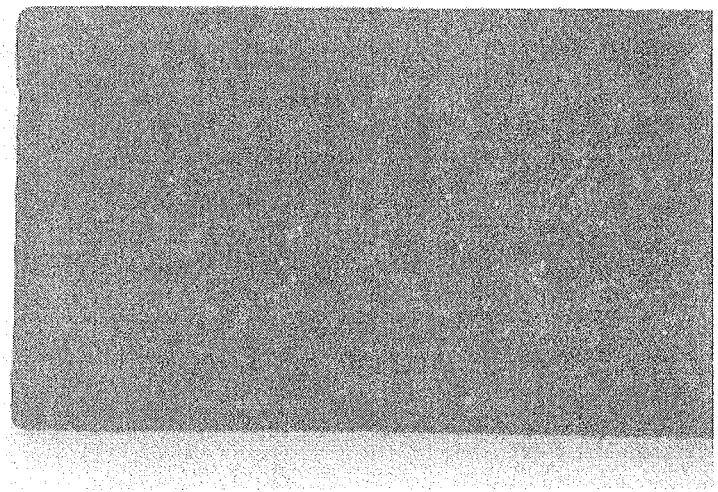
FIG. 2B is an optical microscope photograph showing an appearance after each step when a method for evaluation testing of a material for an internal combustion engine of the present invention is applied, and shows a state of Sample No. 1 after a combustion step.
Figure 2C:
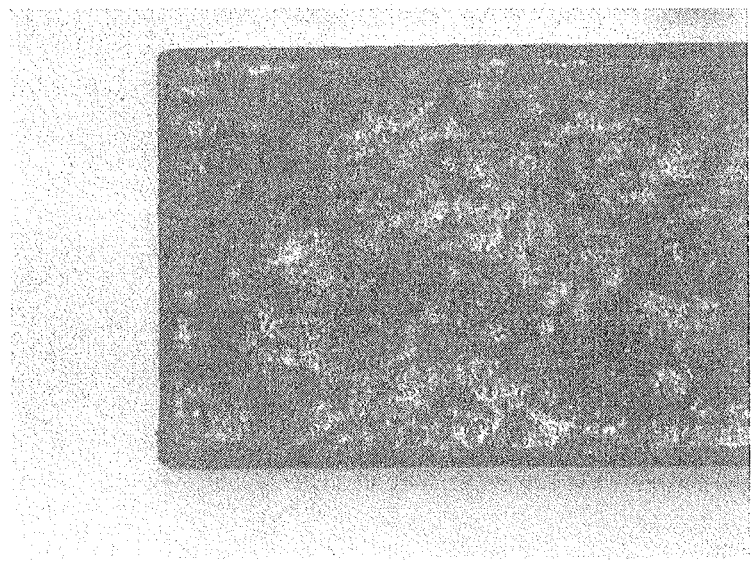
FIG. 2C is an optical microscope photograph showing an appearance after each step when a method for evaluation testing of a material for an internal combustion engine of the present invention is applied, and shows a state of Sample No. 1 after a heating step.
Figure 2D:
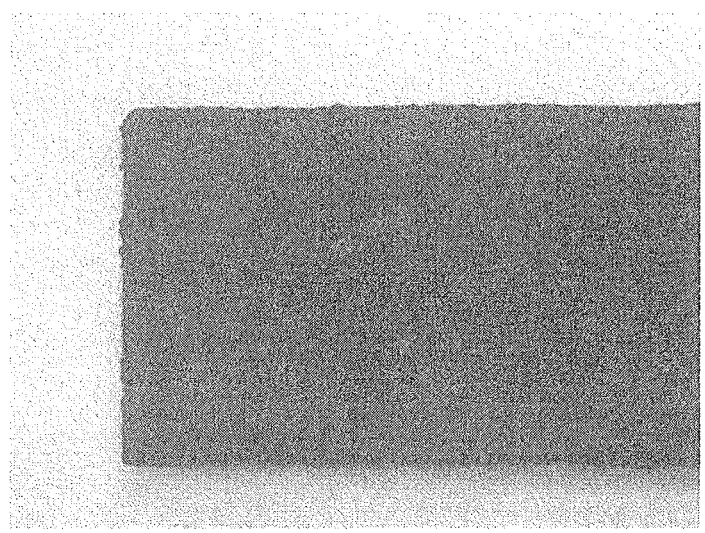
FIG. 2D is an optical microscope photograph showing an appearance after each step when a method for evaluation testing of a material for an internal combustion engine of the present invention is applied, and shows a state of Sample No. 2 after a combustion step.

In the combustion step, the equipment including the explosion-proof enclosure and commercially available engine oil for ships are used as in the step of combustion performed on Sample Nos. 100 and 200. Subsequently, Sample Nos. 1 and 2 (here, the samples washed with water) that had been subjected to the wet etching step were exposed to a flame of the engine oil. In this test, the time during which the samples were exposed to the flame was about 50 milliseconds. After this exposure to the flame, CP cross sections of Sample Nos. 1 and 2 were obtained, and each of the cross sections was observed with an optical microscope. FIG. 1B shows a microscope photograph of the cross section of Sample No. 1 after the combustion step, and FIG. 1E shows a microscope photograph of the cross section of Sample No. 2 after the combustion step. FIG. 2B shows an appearance photograph of Sample No. 1 after the combustion step, and FIG. 2D shows an appearance photograph of Sample No. 2 after the combustion step.

Figure 1F:
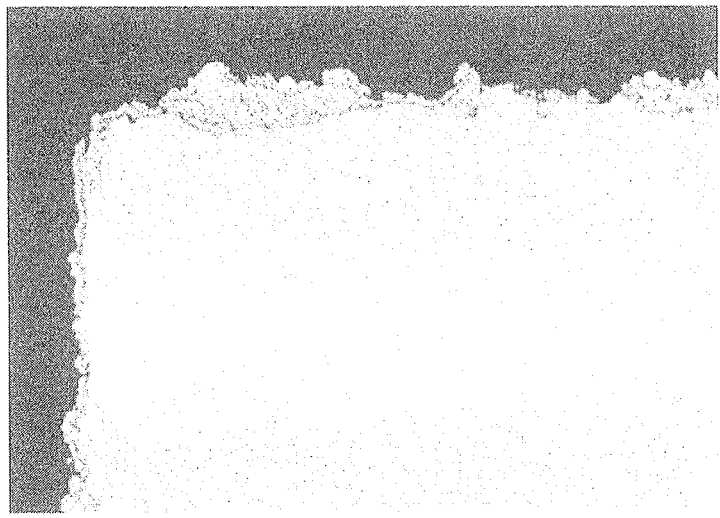
FIG. 1F is an optical microscope photograph of a cross section showing a state after each step when a method for evaluation testing of a material for an internal combustion engine of the present invention is applied, and shows a state of Sample No. 2 after a heating step.

As shown in FIGS. 1A and 1B, with regard to Sample No. 1, a substantial difference in the surface state between before and after the combustion step was not observed, and only an oxide film was present. As shown in FIGS. 1D and 1E, with regard to Sample No. 2, after the combustion step, the oxide film disappeared. Thus, although there is a difference in the state of the oxide film, in each of Sample Nos. 1 and 2, no particles were observed, as shown in FIGS. 2B and 2D. Accordingly, it is difficult to say that the ease of the formation of particles can be appropriately evaluated by simply conducting the combustion step subsequent to the wet etching step. However, from the above results, it was confirmed that a difference in the surface layer region may be generated depending on the type of material, by conducting not only immersion in a corrosive solution or only combustion with a flame of engine oil, but by conducting the combustion step after the wet etching step. In FIG. 1E and FIG. 1F described below, irregularities of the base material of the sample are roughened portions due to cutting, as described above.

Figure 2E:
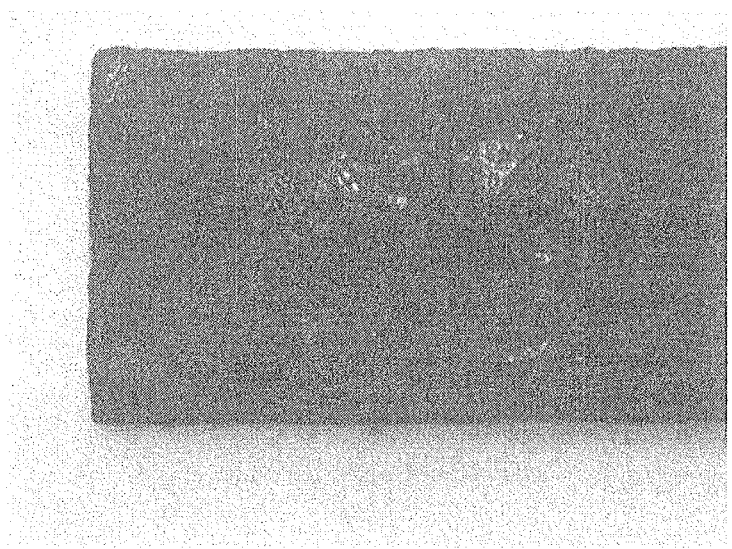
FIG. 2E is an optical microscope photograph showing an appearance after each step when a method for evaluation testing of a material for an internal combustion engine of the present invention is applied, and shows a state of Sample No. 2 after a heating step.

The heating step was conducted by using the vacuum furnace described above in a vacuum atmosphere (oxygen content: 0.01% by volume or less, the degree of vacuum: 50 Pa or less) at 990° C. for 72 hours similarly to the heating step conducted for Sample Nos. 100 and 200. CP cross sections of Sample Nos. 1 and 2 that were subjected to this heating step and then cooled to room temperature were obtained, and each of the cross sections was observed with an optical microscope. FIG. 1C shows a microscope photograph of the cross section of Sample No. 1 after the heating step, and FIG. 1F shows a microscope photograph of the cross section of Sample No. 2 after the heating step. FIG. 2C shows an appearance photograph of Sample No. 1 after the heating step, and FIG. 2E shows an appearance photograph of Sample No. 2 after the heating step.

The comparison between FIGS. 2B and 2C shows that, with regard to Sample No. 1, a plurality of particles are formed on the surface after the heating step and the surface has significant irregularities. In contrast, the comparison between FIGS. 2D and 2E shows that, with regard to Sample No. 2, a significant difference in the surface state is not observed before and after the heating step. The comparison between FIGS. 2C and 2E shows that Sample No. 1 is composed of a material in which particles are easily formed as compared with Sample No. 2. These results show that the test including the steps of wet etching step→combustion step→heating step in that order can be used for evaluating the ease of the formation of particles, with respect to a sample composed of a nickel-based metal.

Figure 3:
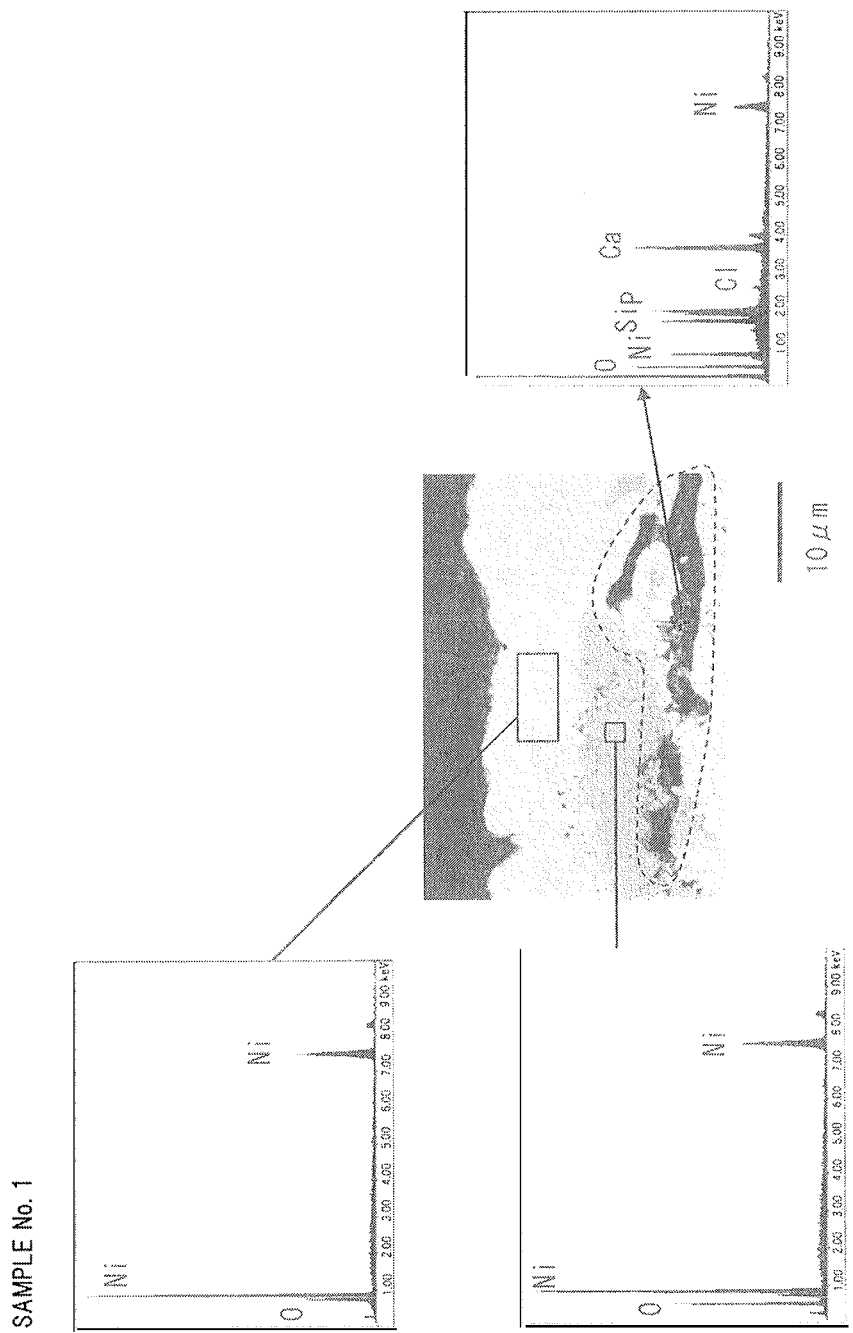
FIG. 3 includes a scanning electron microscope photograph showing a cross section of a surface layer region after a heating step when a method for evaluation testing of a material for an internal combustion engine of the present invention is applied to Sample No. 1, and graphs showing compositions of respective portions of the surface layer region.

In addition, as shown in FIG. 1C, in Sample No. 1, a large number of voids (black granular portions, black portions present in the area surrounded by the broken lines in FIG. 3 described below) are observed in the surface layer region, and a region on the outermost surface side is formed of a structure different from the base material that is constituted by a crystal structure in which fine precipitates and the like are dispersed. Accordingly, the composition of the surface layer region of Sample No. 1 was specifically examined. Here, the component analysis was performed by energy dispersive X-ray spectroscopy. FIG. 3 includes a SEM photograph that shows the surface layer region of Sample No. 1 in an enlarged scale and graphs showing the compositions of respective portions of the surface layer region. As shown in FIG. 3, a region in the vicinity of the voids and a region on the outermost surface side are constituted by not a Ni—Y—Si alloy but substantially only Ni. These results support the occurrence of the following phenomenon. Through the steps including wet etching step→combustion step→heating step, the base material becomes deficient in additional elements (Si and Y in this case), the concentration of Ni in the matrix is increased to form a Ni-enriched phase, and a material containing the Ni-enriched phase as a main component flows to the surface side. In addition, as shown in FIG. 3, in a portion in the vicinity of the voids, elements such as Ca and P, which were contained in the engine oil, were detected and present in relatively high concentrations. These results support the occurrence of the following phenomenon. Through the steps including wet etching step→combustion step→heating step, the Ni-enriched phase contacts components in the engine oil to form a low-melting point phase, and consequently, the low-melting point phase flows to the surface side, includes the components in the engine oil, and forms a compound and the like. Furthermore, the low-melting point phase is believed to be formed as follows. In a cooling step after heating, only Ni is first precipitated, and compounds of Ni and Ca, P, etc. are then precipitated. Through these steps, constituent elements of the low-melting point phase are separated, thereby forming a structure in which a region on the outermost surface side is substantially composed of Ni, and Ca, P, etc. are present inside the outermost surface. Note that Cl (chlorine) in the graph on the right-hand side of FIG. 3 is believed to be attributable to the corrosive solution.

Figure 4:
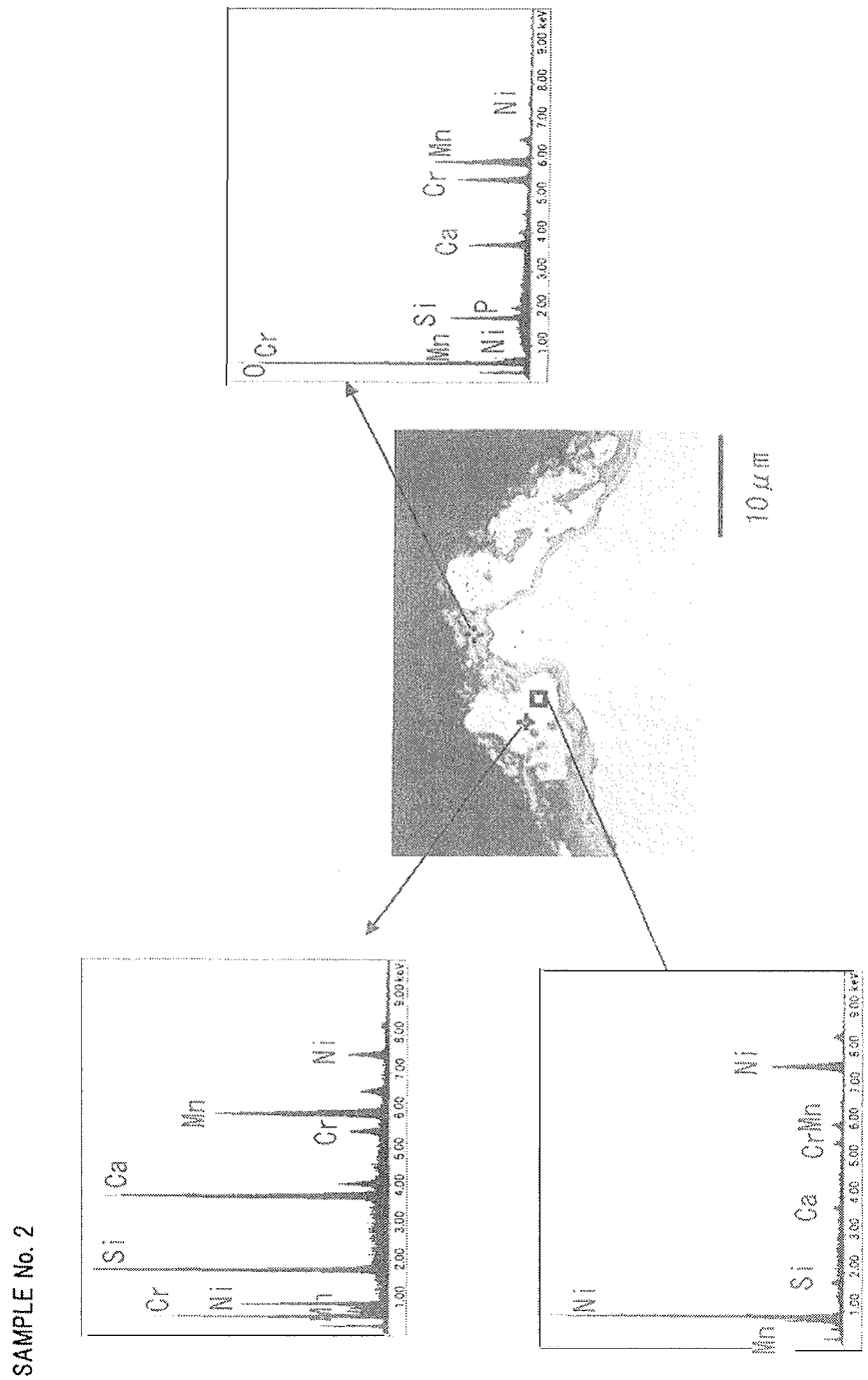
FIG. 4 includes a scanning electron microscope photograph showing a cross section of a surface layer region after a heating step when a method for evaluation testing of a material for an internal combustion engine of the present invention is applied to Sample No. 2, and graphs showing compositions of respective portions of the surface layer region.

On the other hand, as shown in FIG. 1F, in Sample No. 2, voids are not substantially present in the surface layer region, and the structure constituting the surface layer region is different from that of the base material, similarly to Sample No. 1. Accordingly, the composition of the surface layer region of Sample No. 2 was examined as in Sample No. 1. FIG. 4 includes a SEM photograph that shows the surface layer region of Sample No. 2 in an enlarged scale and graphs showing the compositions of respective portions of the surface layer region. As shown in FIG. 4, in Sample No. 2, the surface layer region is constituted by, over the entire region, a mixture formed by chemical combination, composite, or the like of a nickel alloy (Ni—Si—Cr—Mn alloy in this case) of the base material and components (Ca, P, etc. in this case) in the engine oil, though the contents are somewhat different from each other. These results support that, in the material in which particles are not easily formed, even when the steps including wet etching step→combustion step→heating step are performed, a phenomenon in which the Ni-enriched phase is generated, the Ni-enriched phase flows while including the components in the engine oil, and the Ni-enriched phase and the components in the engine oil form a compound substantially does not occur, though the surface layer region is somewhat subjected to a degeneration due to corrosion and heat. That is, through the steps including wet etching step→combustion step→heating step, it is possible to satisfactorily perform selection between materials in which particles are easily formed and materials in which particles are not easily formed.

On the basis of the above results, it was confirmed that the method for evaluation testing of a material for an internal combustion engine of the present invention, the method including immersion in the corrosive solution, combustion with a flame of engine oil, and heating is valid as a method for evaluating characteristics (in particular, the ease of the formation of particles) of a constituent member of an internal combustion engine. It was also confirmed that, according to the method for evaluation testing of a material for an internal combustion engine of the present invention, characteristics (in particular, the ease of the formation of particles) of a constituent member of an internal combustion engine can be evaluated with simple equipment.

The present invention is not limited to the embodiments described above, and various modifications can be appropriately made without departing from the gist of the present invention. For example, the material, the shape, etc. of a sample, the conditions for the wet etching step (the composition of the corrosive solution, the temperature, the immersion time, etc.), the conditions for the heating step (the temperature, the holding time, the atmosphere, etc.), the conditions for the heat treatment step (the temperature, the holding time, the atmosphere, etc.), and the like can be appropriately changed. The heat treatment step may be omitted.

Furthermore, it is expected that the method for evaluation testing of a material for an internal combustion engine of the present invention can be applied to not only nickel-based metals but also metal materials which are used as a material of an internal combustion engine and in which particles may be generated on a surface by use over time, for example, aluminum alloys and steels. In such a case, test conditions such as the concentration of an acid in the corrosive solution and the heating temperature in the heating step are preferably adjusted depending on the type of material.

INDUSTRIAL APPLICABILITY

The method for evaluation testing of a material for an internal combustion engine of the present invention can be suitably used for evaluating the ease of the generation of particles, with respect to a nickel-based metal material constituting a member included in various internal combustion engines such as gas engines and gasoline engines of automobiles (typically, four-wheeled vehicles and two-wheeled vehicles). In addition, according to the method for evaluation testing of a material for an internal combustion engine of the present invention, the ease of the generation of particles can be evaluated by using a sample in the form of either an electrode or a raw material before being formed into an electrode. Therefore, the method can also be suitably used for selection of materials in which particles are not easily generated.

The invention claimed is:

1. A method comprising:
    a wet etching step of preparing, as a metal material, a sample composed of a nickel-based metal, preparing, as a corrosive solution, an aqueous solution containing an acid and sodium chloride, and immersing the sample in the corrosive solution to form a Ni-enriched phase in a surface layer region of the sample;

a combustion step of exposing the sample that has been immersed in the corrosive solution to a flame of engine oil so that the Ni-enriched phase is brought into contact with a component in the engine oil to form a low-melting point phase in the surface layer region of the sample; and a heating step of heating the sample that has been exposed to the flame of the engine oil to melt the low-melting point phase and resolidifying the low-melting point phase.

2. The method according to claim 1, wherein the heating step is performed in a non-oxidizing atmosphere at a heating temperature of 450° C. or more and less than 1,455° C. for a holding time of 1 hour or more and 100 hours or less.

3. The method according to claim 1, wherein, in the wet etching step, a solution containing at least one acid selected from hydrochloric acid, phosphoric acid, nitric acid, and sulfuric acid is prepared as the corrosive solution, and an immersion time of the sample is 2 hours or more and 48 hours or less.

4. The method according to claim 1, further comprising:

before the wet etching step, a heat treatment step of performing heat treatment on the sample, wherein, in the heat treatment step, a heating temperature is 800° C. or more and 1,100° C. or less, and a holding time is 1 hour or more and 200 hours or less.

\* \* \* \* \*